United States Patent [19]

Clavell, Jr.

[11] 4,097,680

[45] Jun. 27, 1978

[54] SPINNING DISK ELECTRICAL ISOLATOR FOR A FLOWING SEAWATER STREAM

[75] Inventor: Cesar Clavell, Jr., San Diego, Calif.

[73] Assignee: The United States of America as represented by the Secretary of the Navy, Washington, D.C.

[21] Appl. No.: 776,144

[22] Filed: Mar. 10, 1977

[51] Int. Cl.² .......................................... H01B 17/00
[52] U.S. Cl. ...................................... 174/8; 137/391; 137/566
[58] Field of Search ................... 174/8, 9 F; 137/386, 137/391, 566; 222/64, 255; 417/246, 247, 420, 426

[56] References Cited

U.S. PATENT DOCUMENTS

| | | | |
|---|---|---|---|
| 2,386,505 | 10/1945 | Puchy | 417/420 |
| 2,616,950 | 11/1952 | Terpstra | 174/9 F X |

Primary Examiner—Laramie E. Askin
Attorney, Agent, or Firm—Richard S. Sciascia; Ervin F. Johnston; Thomas Glenn Keough

[57] ABSTRACT

A pair of pumps driven by a common motor draw in ambient seawater through one and expel it through the other to following electronic instrumentation. Coupled between the pumps, a rapidly rotating disk receives the flow of seawater and radially dissipates it in a multitude of separated droplets. The droplets are collected in a reservoir and the second pump expels it to the instrumentation. Where the flowing seawater is separated into droplets by the rapidly spinning disk, a break is created in the electrical conductivity continuity so that the following electronic instrumentation is not influenced by possible electrical potentials in the ambient seawater.

10 Claims, 3 Drawing Figures

SPINNING DISK ELECTRICAL ISOLATOR FOR A FLOWING SEAWATER STREAM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

A number of electronic sensors and related devices currently are being used to monitor a variety of phenomena in flowing solutions. Since readings can be altered by outside influences, electrical isolation of the sensing instrumentation is frequently employed. A usual practice is to fill a container full of the solution and perform an analysis. However, this approach usually requires a full-time technician and the process itself is unduly time consuming. With the increased interest being shown to environmental factors, such as air and water pollution, long-term monitoring by these techniques is not practical. To facilitate the automation of electrochemical analysis techniques, instruments are being configured so as to operate on a continuously flowing medium. Thus, there is a continuing need in the state-of-the-art for an apparatus that will separate test instrumentation from base potentials which may be conducted through a flowing fluid sample.

SUMMARY OF THE INVENTION

The present invention is directed to providing an apparatus for breaking the electrical conductivity continuity in a fluid flowing from a source to instrumentation. A means is coupled to the source of the fluid for impelling fluid onto a means which radially dissipates the fluid in a form of a multitude of separated droplets. A means collects the droplets for coalescing them into a reservoir of fluid which is expelled by an expelling means to feed the fluid to the following instrumentation. Both the impelling means and the expelling means are driven by a synchronous driving means to match the flow rates to and from the reservoir of fluid and thereby ensure the breaking of the electrical conductivity continuity.

OBJECTS OF THE INVENTION

It is an object of the invention to provide an apparatus which isolates instrumentation from the residual potentials in a flowing fluid.

Another object is to provide an apparatus employing a spinning disk which radially dissipates fluid to effect an electrical isolation.

Still another object is to provide an apparatus by which an electrical isolation is assured by a pair of commonly driven pump heads.

Still another object is to provide an apparatus employing an inductively driven spinning disk to further assure electrical isolation.

These and other objects will become more readily apparent from the ensuing description when taken with the drawings.

DESCRIPTION OF THE PREFERRED EMBODIMENT

Figure 1:
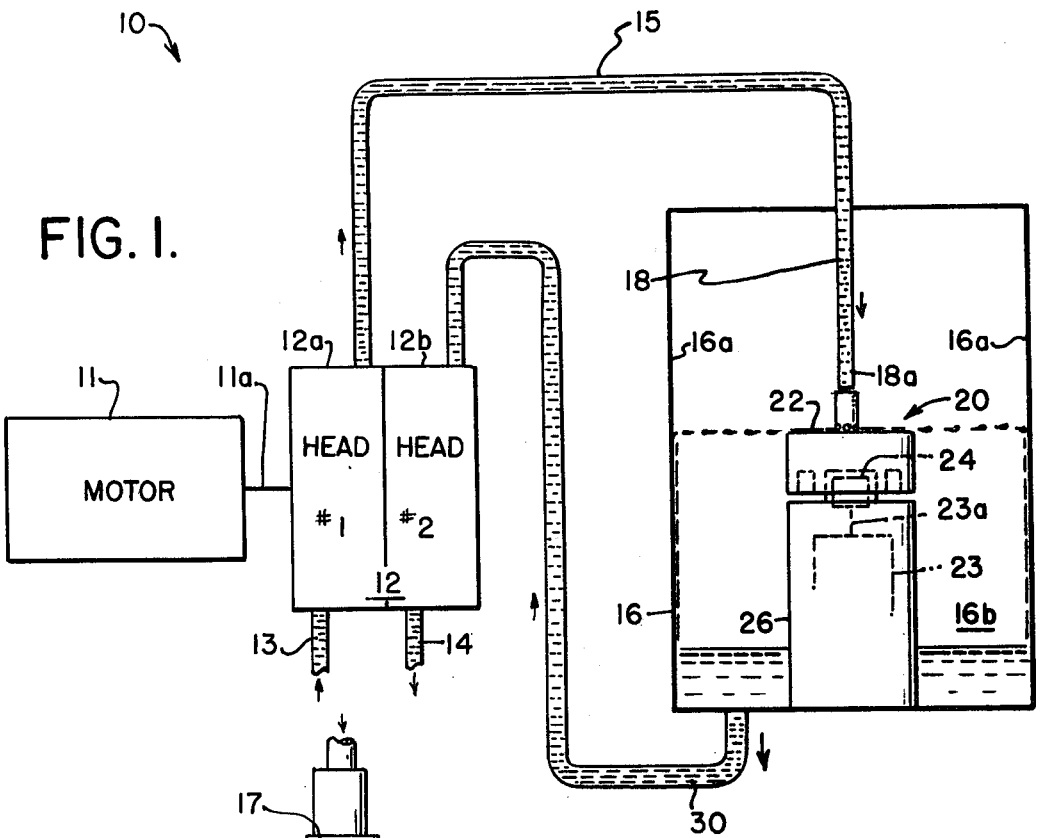
FIG. 1 depicts a schematic representation of the invention partially in cross section.

Referring now to the drawings, a representative embodiment of an electrical isolator 10 has a motor 11 driving a two-headed pump 12. The pump is a commercially available unit such as a model 75-45 marketed by Cole-Parmar Corporation of Chicago, Illinois. In each head 12a or 12b peristalic tubings feed approximately 250 milliliters per minute through the pump in opposite directions. May it be emphasized at this point that a common drive shaft 11a actuates heads 12a and 12b to deliver identical flow volumes in opposite directions through pump 12. This feature assures that there is an electrical isolation between the fluid at an input section of tubing 23 and the fluid in an output section of tubing 14.

A fluid, in this case seawater, is drawn through the input section of tubing 13 by head 12a of the two-headed pump. It is pumped through a section of tubing 15 and is fed to a sealed chamber 16 through an inlet fitting 17.

Figure 2:
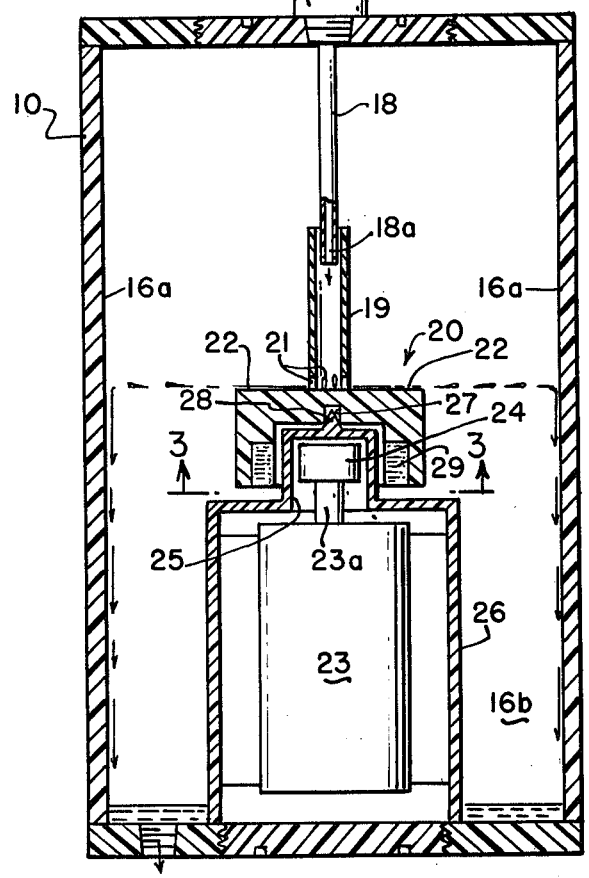
FIG. 2 is a cross-sectional representation of a portion of the invention.
Figure 3:
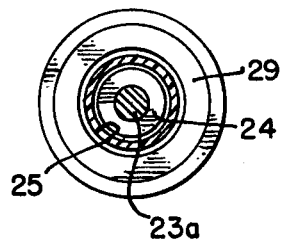
FIG. 3 is a cross-sectional representation of the invention taken generally along line 3—3 in FIG. 2.

Looking more specifically to FIG. 2, a section of pipe 18 extends inwardly from the inlet fitting. Its innermost end 18a is journaled in a cylindrical section 19 of a spinning disk assembly 20.

The disk assembly includes the aforementioned cylindrical section which is provided with a number of openings 21 at its lower end. The openings permit fluid to flow onto a disk surface 22.

The fluid is dissipated in a multitude of discrete droplets from the disk surface as the disk assembly is rotated rapidly by a motor 23. A motor shaft 23a spins a cylindrical driving magnet 24 inside of a cup-shaped recess 25 formed in a fluid-tight housing 26.

The spinning disk assembly is provided with a small hole 27 into which a spur 28 from housing 26 is fitted. An annular driven magnet 29 is mounted on the underside of the spinning disk. The driven magnet has a polarity such that rotation of driving magnet 24 will cause the driven magnet to follow it about the axis defined by shaft 23a and the hole and spur.

An outflow section of tubing 30 is connected to the bottom side of chamber 16 and feeds fluid through two-headed pump 12. Head 12b draws the fluid through the outflow of section of tubing and discharges it through an output section of tubing 14 to the instrumentation. Again, may it be reemphasized that the flow rates through the two heads 12a and 12b are equal but in opposite directions so that there cannot be an over accumulation of fluid inside chamber 16. This feature has been included to prevent the possibility of having the fluid level rising above disk surface 22 to create an electrically conductive path between the fluid in the input section of tubing 13 and the fluid in the output section of tubing 14.

In operation, ambient seawater is brought in through the input section of tubing by head 12a of the pump. It passes through tubing section 15 into chamber 16. Motor 23 rapidly spins driving magnet 24 and since driven magnet 29 is inductively coupled to the driving magnet, the disk assembly 20 is rapidly spun. Seawater coming through pipe 18 and cylindrical section 19 is forced through openings 21 by centrifugal force, the rapidly moving disk surface 22 dissipates the fluid in the form of a multitude of separated droplets. Between the periphery of disk surface 22 and the inner walls 16a a gap is created in the flowing fluid due to the separation between the multitude of droplets. The fluid is collected on the inner walls of the chamber and flows to a reservior section 16b in the chamber. Head 12b, pumping an equal volume but in an opposite direction as 12a, draws fluid from the reservoir via outflow section of tubing 30 to discharge it through the output section of tubing 14.

From the foregoing it is apparent that the electrical isolator does in fact disrupt the electrical conductivity continuity in a fluid flowing from a source to electronic instrumentation. Since the motor 23 is contained within a housing 26 and there is inductive coupling between magnets 24 and 29, volatile or otherwise reactive fluids can be handled safely by the electrical isolator. Because the flow in and the flow out are the same by reason of the two-headed pump 12, higher reliability is assured. Fabricating all the sections of the tubing, chamber spinning disk assembly and the pumps from nonreacting materials guarantees long trouble-free operation.

Obviously, many modifications and variations of the present invention are possible in the light of the above teachings, and, it is therefore understood that within the scope of the disclosed inventive concept, the invention may be practiced otherwise than as specifically described.

What is claimed is:

1. An apparatus for breaking the electrical conductivity continuity in a fluid flowing from a source to instrumentation comprising:

drivable impelling means coupled to the source for impelling the fluid therefrom;

means coupled to the impelling means for radially dissipating the fluid in the form of a multitude of separated droplets;

means arranged to collect the multitude of separated droplets for coalescing them into a reservoir of fluid;

drivable expelling means coupled to the reservoir of fluid for expelling the fluid therefrom and to the instrumentation; and means connected to the drivable impelling means and drivable expelling means for synchronously driving them thereby matching the flow rates to and from the reservoir of fluid.

2. An apparatus according to claim 1 further including:

means connected to the drivable impelling means for receiving the fluid therefrom.

3. An apparatus according to claim 1 further including:

means coupled to the radially dissipating means for imparting rotational motion thereto.

4. An apparatus according to claim 3 in which the rotational motion imparting means is a motor localed in a fluid-tight housing disposed in the fluid reservoir.

5. An apparatus according to claim 4 in which the rotational motion imparting means is inductively coupled to the radially dissipating means.

6. An apparatus according to claim 5 in which the radially dissipating means is a disk rotatably mounted on the outside of the fluid-tight housing.

7. An apparatus according to claim 6 in which the synchronously driving means is a motor having its drive shaft connected for simultaneously driving the drivable impelling means and drivable expelling means.

8. An apparatus according to claim 7 in which the drivable impelling means and drivable expelling means are a pair of pump heads having a substantially identical pumping capability.

9. An apparatus according to claim 8 in which the receiving means is a length of tubing coaxially mounted on the disk and having a number of openings near the surface of the disk for feeding fluid therethrough.

10. An apparatus according to claim 9 in which the flow rate of the fluid is controlled by the pair of pump heads to permit an effective radial dissipation of the fluid by the disk.

* * * * *